United States Patent [19]

Holtkamp

[11] Patent Number: Plant 5,616

[45] Date of Patent: Dec. 31, 1985

[54] AFRICAN VIOLET PLANT NAMED IMPROVED WASHINGTON

[75] Inventor: Reinhold Holtkamp, Isselburg, Fed. Rep. of Germany

[73] Assignee: Gessellschaftsvertrag uber die Ergindergemeinschaft "Optimara", Fed. Rep. of Germany

[21] Appl. No.: 568,448

[22] Filed: Jan. 5, 1984

[51] Int. Cl.[4] ..... A01H 5/00

[52] U.S. Cl. ..... Plt./69

[58] Field of Search ..... Plt./69

*Primary Examiner*—Robert E. Bagwill

*Attorney, Agent, or Firm*—Schwartz, Jeffery, Schwaab, Mack, Blumenthal & Koch

[57] ABSTRACT

A new and distinct cultivar of African violet plant named Improved Washington characterized by its intense violet blue flower color and single to semi-double frilled flower shape, an abundance of strong and upright flower stems, each of which carry 9 or more flowers thereby making the cultivar highly floriferous, vigorous and compact growth habit, and by its yellow and prominent pollen, which provides a pleasing contrast to the flower color.

1 Drawing Figure

The present invention comprises a new and distinct cultivar of African violet plant, botanically known as *Saintpaulia ionantha,* and named Improved Washington.

The new cultivar was referred to during the breeding and selection process by the designation E 47/3 semi-double blue frilled, and is a product of a planned breeding program. The basic objective of the breeding program was to create an African violet cultivar improving in several important respects the characteristics of the cultivar Washington, a commercially introduced but unpatented cultivar.

The new cultivar was originated from a cross made in a controlled breeding program in Isselburg, West Germany. The female, or seed parent was a cultivar designated B 318/13 blue single. The male, or pollen parent was a cultivar designated D 4/6 blue frilled.

The new cultivar Improved Washington was discovered and selected by me as a flowering plant within the progeny of the stated cross in a controlled environment in Isselburg, West Germany. Asexual reproduction of the new cultivar by leaf cuttings and by division of shoots, as performed by me at Isselburg, West Germany, has demonstrated that the combination of characteristics as herein disclosed for the new cultivar are firmly fixed and are retained through successive generations of asexual reproduction.

Improved Washington has not been observed under all possible environmental conditions. The phenotype may vary significantly with variations in environment such as temperature, light intensity and day length. The following observations, measurements and values describe the new cultivar as grown in Isselburg, West Germany and Nashville, Tenn. under greenhouse conditions which closely approximate those generally used in commercial practice.

The following traits have been repeatedly observed and are determined to be basic characteristics of Improved Washington, which in combination distinguish this African violet as a new and distinct cultivar:

1. Vigorous growth habit.
2. Strong and upright flower stems, with 7-9 and more stems being produced.
3. Semi-double flowers which are an intense dark purple and frilled at the edges.

4. Profuse flowering, with 9 or more flowers being carried on each stem.
5. Compact growth habit.
6. The prominent yellow pollen provides a very pleasant contrast with the intense dark purple flower color.

The new cultivar can be compared with the cultivar Washington but is considered an improvement with regard to several important characteristics. Improved Washington has a more intense dark purple color, produces more and stronger stems is more compact, and is more floriferous, with 9 or more flowers being carried on each stem.

The accompanying photographic drawing shows a typical specimen plant of the new cultivar. The color appearing in the photograph are as true as possible with color illustrations of this type.

In the following description, color references are made to The Royal Horticultural Society Colour Chart (R.H.S.), except where general colors of ordinary significance are referred to. Color values were taken under natural light conditions at approximately mid-day in Nashville, Tenn. When the cultivar is grown under cooler conditions, the color will be slightly more intense, and relatively high finishing temperatures will result in some color fading.

Botanical classification: *Saintpaulia ionantha,* Ramat. cv. IMPROVED WASHINGTON.

Parentage:

*Male parent.*—D 4/6 blue frilled.

*Female parent.*—*B* 318/13 blue single.

Propagation: The new cultivar holds its distinguishing characteristics through successive propagations by leaf cuttings and by division of shoots.

Plant: From 6 cm. to 8 cm. tall when grown in pots, and approximately 25 cm. in diameter when fully grown.

*Leaves.*—General form: Oval to heart shape. Diameter: 65-70 mm. Texture: Leather-like. Aspect: Variety, hairy, slightly shiny and serrated. Veins: Pronounced. Color (upperside): Yellow green 147A. Color (underside): Yellow green 148D.

*Flowers.*—Buds: Ball shaped, purplish brown in color. Sepals: Spear shape. Color: Brownish green. Calyx: Flat funnel shape. Peduncle: Short and brownish green; very hairy.

*Individual flowers.*—Size: 35–40 mm. Color: Upperside: Violet blue Group between 89B-C. Underside: Violet Group 88C. Borne: Upright on short peduncles. Shape: Violet shape with 2 small and 3 large petals; additional petals frequently appear out of the center; single to semi-double flowers. Corolla: Compact flower head, free above the leaves. Flowering time: A full bouquet appears 8–10 weeks after potting.

*Reproductive organs.*—Anthers: Two composed of four anther cells, seed capsules pushed slightly through; anthers cells are carried by dark purple stems. Styles: Dark purple yellow turning to light green at the ovary. Pollen color: Yellow.

*Roots.*—White when young and active; brownish when older.

*Disease resistance.*—Good as experienced to date.

General observations:

Improved Washington is a very attractive plant. An abundance of strong, upright and wire-like stems carry many dark purple frilled single to semi-double flowers thereby making the cultivar very floriferous. The stems curve slightly to the center to form a very compact flower head centrally above the leaves. The plant is very productive, achieving in 8–10 weeks after potting a saleable plant having a full bouquet.

I claim:

1. A new and distinct cultivar of African violet plant named Improved Washington, as illustrated and described, and particularly characterized by its intense violet blue flower color and single to semi-double frilled flower shape; an abundance of strong and upright flower stems, each of which carry 9 or more flowers thereby making the cultivar highly floriferous; vigorous and compact growth habit, and by its yellow and prominent pollen, which provides a pleasing contrast to the flower color.

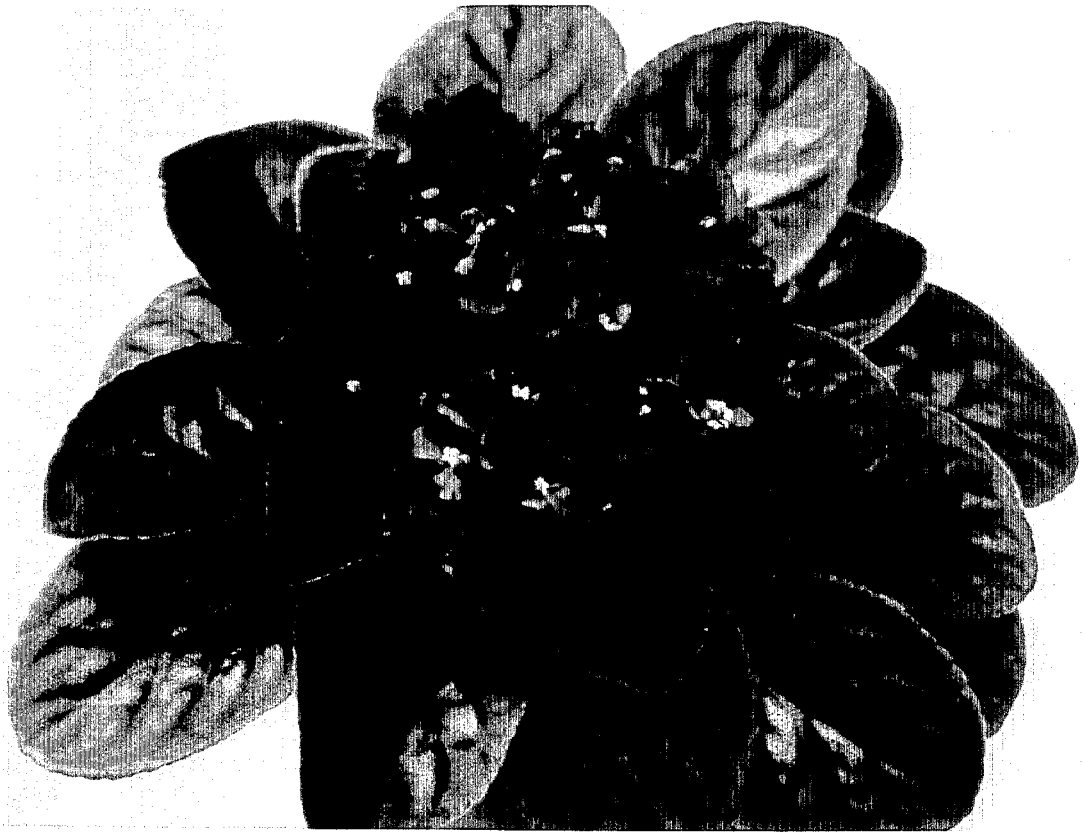

* * * * *